United States Patent
Weinsdorfer et al.

(10) Patent No.: US 6,303,938 B1
(45) Date of Patent: Oct. 16, 2001

(54) METHOD AND DEVICE FOR DETECTION OF UNTEXTURED YARN SECTIONS IN TEXTURED FILAMENT YARNS

(75) Inventors: Helmut Weinsdorfer, Pliezhausen (DE); Beiheng Cui, Stoney Creek (CA)

(73) Assignees: Deutsche Institute fur Textil-und Faserforschung, Stuttgart; Stiftung des Offentlichen Rechts, Donkendorf, both of (DE)

( * ) Notice: Subject to any disclaimer, the term of this patent is extended or adjusted under 35 U.S.C. 154(b) by 0 days.

(21) Appl. No.: 09/171,026
(22) PCT Filed: Apr. 7, 1997
(86) PCT No.: PCT/EP97/01729
§ 371 Date: Jun. 28, 1999
§ 102(e) Date: Jun. 28, 1999
(87) PCT Pub. No.: WO97/38306
PCT Pub. Date: Oct. 16, 1997

(30) Foreign Application Priority Data

Apr. 9, 1996 (DE) .............................................. 196 14 027

(51) Int. Cl.$^7$ .................................................. G01N 21/00
(52) U.S. Cl. ................................ 250/559.27; 250/559.45; 250/559.13; 250/559.15; 250/559.19; 356/430; 356/238.2; 340/677; 57/264; 57/265; 73/570
(58) Field of Search ................................ 73/570, 649, 651, 73/862.381, 862.391, 862.41, 160; 57/264, 265; 310/323, 330; 340/677, 679, 668; 356/429, 430, 238.1–238.3; 250/559.01, 559.12, 559.13, 559.15, 559.19, 559.27, 559.2, 559.45

(56) References Cited

U.S. PATENT DOCUMENTS

| | | | |
|---|---|---|---|
| 3,879,660 | * | 4/1975 | Piso .......................................... 324/61 |
| 4,274,746 | * | 6/1981 | Cardell et al. ........................ 356/429 |
| 4,295,360 | | 10/1981 | Fountain ............................... 73/15.6 |
| 4,677,860 | * | 7/1987 | Wessolowski et al. ........... 73/862.48 |
| 4,812,043 | * | 3/1989 | Vanstaen .............................. 356/385 |
| 5,119,308 | * | 6/1992 | Samoto ................................ 364/470 |
| 5,136,202 | * | 8/1992 | Carenzo et al. ..................... 310/330 |
| 5,164,710 | * | 11/1992 | Anderegg et al. .................. 340/677 |
| 5,329,822 | * | 7/1994 | Hartel et al. ....................... 73/862.61 |
| 5,705,817 | * | 1/1998 | Louis et al. ........................ 250/359.1 |
| 6,038,021 | * | 3/2000 | Piso et al. .......................... 356/238.2 |

FOREIGN PATENT DOCUMENTS

| | | |
|---|---|---|
| 4119780 | 1/1992 | (DE) . |
| 0495445 | 9/1992 | (EP) . |
| 0531753 | 3/1993 | (EP) . |
| 0555639 | 8/1993 | (EP) . |

* cited by examiner

Primary Examiner—Hezron Williams
Assistant Examiner—Rose M. Miller
(74) Attorney, Agent, or Firm—Pandiscio & Pandiscio

(57) ABSTRACT

A method for detecting untextured or defectively textured yarn segments in textured filament yarns during the texturing process, in which the textured yarn is continuously measured by the measurement, conditioning and evaluation of high-frequency measurement signals as evidence of untextured or defectively textured yarn segments.

22 Claims, 6 Drawing Sheets

Figure 1:
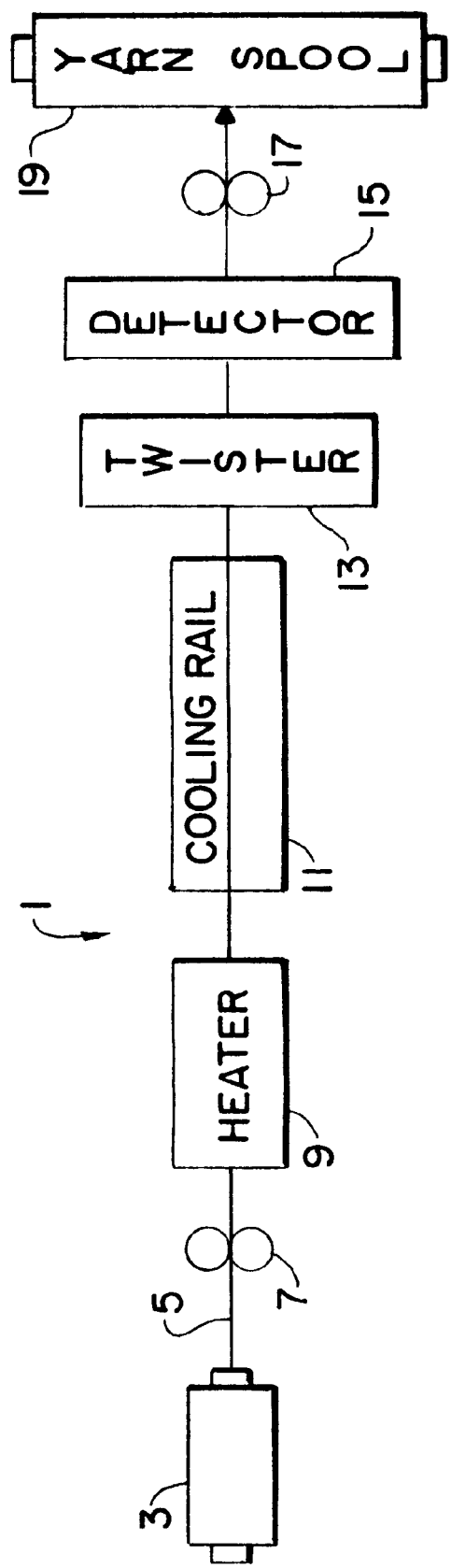

METHOD AND DEVICE FOR DETECTION OF UNTEXTURED YARN SECTIONS IN TEXTURED FILAMENT YARNS

The invention concerns a method for detecting untextured or defectively textured yarn segments in textured filament yarns during the texturing process and a device for carrying out this method.

The texturing of filament yarns, particularly multifilament yarns, is known. Texturing serves to a produce from a synthetic, flat and smooth multifilament yarn a crimped and structured yarn that has textile character because of its bulky and lofty structure. For this purpose, the multifilament yarn is generally unwound from a spool, guided through a first delivery device, then heated in a heater, cooled on a cooling rail, and guided through a twister and a second delivery device arranged thereafter, a so-called draw-off delivery device, ultimately to be wound onto a yarn spool. The twister serves to temporarily impart high torque to the multifilament yarn in one pass (temporary torque is also known as false twist) and makes it possible, by means of the residual torque that simultaneously develops, to heat-set the twisted state by heating and cooling in the region ahead of the twister. After the twister, the torque is removed again and the filament yarn is untwisted. Because of the heat-setting treatment effected in the twisted state, the yarn has the desired crimped structure.

The torque is imparted primarily with a three-shaft disk friction unit or by means of so-called crossed belts. The use of friction to impart the torque permits very high rotation speeds and thus also high production speeds. However, if the friction ratios between the twister and the yarn are not constant, this leads to disruptions of the process that are also known as instabilities, and thus to loss of quality in the yarn. Such defects can result from spinning problems, uneven application or distribution of the spinning preparation on the surface of the yarn, temperature fluctuations during texturing or contamination by the heating and/or cooling rails. Such disruptions can cause so-called ballooning of the yarn, which occurs in particular at high rotation speeds. Ballooning of the yarn causes uncontrolled travel of the yarn, fluctuations of the yarn tension, and losses of quality. In unstable processes, in particular, the yarn can skip across the surfaces of the disks in the friction unit. This so-called "closing up" of the twist[1] causes a torque deficit in the twist zone. Yarn that has been imparted high torque before the twister can therefore pass through the unit briefly or by segments without the torque being removed. This results in short untextured yarn segments (temporary twist slippage), so-called tight spots, and long untextured yarn segments ("surging," prolonged twist slippage).

[1]TRANSLATOR'S NOTE: German Drallschluß. Schluß can also be translated as "termination."

The quality of the textured yarn is generally monitored by spot-check-type inspection of the finished textured yarn. Only a very small fraction of the total output can be inspected in this way. In recent years, so-called on-line production controls have been introduced in texturing, with the result that nearly the entire output can be monitored for quality. However, the yarns are not examined by the measuring equipment in an uninterrupted manner, since the measuring sensors and scanning rates used operate at low frequencies, and undesirable short tight spots thus often go undetected. On-line control in the texturing process is generally accomplished by measuring the yarn tension. Known are monitoring systems that are able to detect low-frequency fluctuations[2] and peaks of yarn tension, i.e., fluctuations of yarn tension that are due to relatively long defects in the yarn. These systems are unable to detect short malfunctions and defects.

[2]TRANSLATOR'S NOTE: The German actually says "thread tension pivots" or perhaps "changes in the direction of thread tension" (Fadenzugkraftschwenkungen). We assume that this is a typographical error for "fluctuations of thread tension" (Fadenzugkraftschwankungen), there being only a one-letter difference.

A yarn tension sensor for a textile machine has been disclosed (EP 0 531 753 A1) for the determination of short-period fluctuations of yarn tension. This device is intended to measure relatively high-frequency fluctuations of yarn tension—of up to 50 Hz, for example—at high yarn speeds. It can also, therefore, detect relatively high-frequency fluctuations of yarn tension caused by the displacement of the yarn. This is intended to give the yarn tension sensor a much broader field of application. Examples of such applications that are disclosed include the compensation of aperiodic fluctuations of yarn tension via yarn braking means, the generation of trouble signals in response to periodically occurring deviations from the specified yarn tension characteristic, and detection of the gradual increase in yarn tension that occurs when the last third of a cop is being wound at the spool location, with appropriate throttling of the winding speed to prevent breakage of the yarn.

German Patent Application (Unexamined) 41 19 780 proposes, for quality monitoring in a false-twist crimping machine, measuring the yarn tension continuously between the false-twister and the exit delivery device from the texturing zone. The mean of the measurement values is constantly taken and the position of this mean and/or the relative position of the current measurement value with respect to the mean is evaluated. To permit a statement regarding the nature of the defects that affect quality, it is further proposed to determine a plurality of means differing with respect to the length of the evaluation time and, in order to generate a quality signal, to determine the relative position of the measurement value with respect to one or more of the means and/or the relative positions of the means with respect to one another. However, this method comprising taking the mean is unable to specifically and independently detect and evaluate sudden, brief irregularities in the process, such as voltage peaks, which occur, for example, in the event of hindrances to the winding of the yarn onto the spool and which subsequently disappear completely.

EP 0 406 736 B1 also proposes monitoring the tension of a traveling yarn by the uninterrupted determination of the mean. A difference from the mean and the current yarn tension are also constantly determined. Whenever the mean and/or the difference pass out of prescribed tolerance ranges for set periods of time, corresponding alarm signals are generated. Quality data for the yarn are derived on the basis of the occurrence of such alarm signals during preset time intervals. However, time delay elements with time constants of about 10 milliseconds are used to filter out output signals caused by brief disturbances in the yarn texturing process that are classed as irrelevant.

The technical problem underlying the present invention is, therefore, to provide an improved method, performed during texturing, for detecting undesired, untextured or defectively textured yarn segments, in particular short lengths in filament yarns manufactured in particular by the friction false twist process.

The solution to the technical problem lies in the provision of a method according to the main claim, in particular a method for detecting untextured or defectively textured yarn segments in textured filament yarns during the texturing process, in which high-frequency yarn signals, in particular yarn tension signals, are measured and evaluated. The measured yarn signals permit statements as to the degree and evenness of crimping of the yarn. Tight spots in the yarn, particularly short, untextured tight spots, are determined, by the detection process effected during the texturing process, as correspondingly brief signals which according to the invention are measured and evaluated as evidence of such tight spots. In the context of the present invention, a short tight spot is understood to be a tight spot with a length of no more than approximately 50 mm, preferably 1 to 50 mm. In the context of the present invention, high-frequency yarn tension signals are understood to be peaks or fluctuations of yarn tension which at a given yarn speed have a frequency of more than 0.2 kHz, preferably of 1 to 6 kHz, but also higher frequencies.

The method according to the invention provides in particular that high-frequency yarn tension signals are measured, conditioned and evaluated, thereby permitting statements as to the degree and evenness of crimping of the yarn. Since the method according to the invention detects high-frequency yarn tension signals, it is also able to register, in particular, brief disruptions caused by so-called tight spots, making it possible to detect at an early stage—i.e., before a tangible decline in yarn quality—when a texturing process is unstable and is therefore subject to error.

The invention provides preferably that the yarn tension of the textured yarn is measured after the yarn passes through the twister, i.e., in a state in which the yarn is essentially untwisted again. The performance of the method according to the invention with untwisted yarn, i.e., after passage through the twister, is especially advantageous, since the imparting of the twist and thus the texturing process are not adversely affected by the diversion of the yarn to the sensor that must be done in order to measure the yarn tension.

In a preferred embodiment, the detection method according to the invention is used during the friction false-twist process. The twister in this case is a disk friction unit.

The detection according to the invention of brief disturbances that occur during the texturing process, in particular high-frequency yarn tension signals, is made possible by a measuring sensor able to pick up high-frequency fluctuations or peaks of the yarn tension. The measured high-frequency yarn tension signals are conditioned and evaluated and thus provide information according to the invention concerning the degree and evenness of crimping of the yarn. The evaluation of the measured yarn tension signals is performed, for example, by setting a threshold value and detecting the number of times this threshold is exceeded per time unit. The number of excursions is a measure of irregularities and disturbances. The magnitude of the mean is a relative measure of the intensity of crimping of the yarn.

The method according to the invention therefore permits, in an advantageous manner, the detection in particular of short tight spots that are detected by the measurement of high-frequency yarn (tension) signals.

The invention also concerns a device for detecting untextured or defectively textured yarn segments in textured filament yarns, in particular for the carrying out of the aforesaid method, the device comprising a measuring sensor, a device for signal conditioning and processing and for signal analysis, data processing and potentially data output, and the measuring sensor being able to detect brief yarn tension signals and deliver them for data evaluation. The evaluation is performed by a device according to the invention, in that its signal processing device can comprise means for selectable smoothing or filtration, determination of the mean, construction of scattering matrices, determination of differentials, selectable setting of threshold values and/or counting of the number of times the threshold is exceeded in the conditioned signal, in which case the last counting circuit detects the number of signal readings that exceed the threshold value within a set period of time. The number of readings per time unit is to be considered a measure of the unevenness of crimping of the yarn. The device according to the invention therefore permits the detection of high-frequency yarn signals, in particular yarn tension signals, and their subsequent evaluation, taking into account the relationship, recognized according to the invention, between the occurrence of brief tight spots and that of high-frequency yarn signals. The measuring sensors to be used according to the invention are, in particular, able to pick up yarn tension signals in a frequency range of up to 6 kHz or in even higher frequency ranges.

The measured high-frequency yarn signals can then, for example, be evaluated further by FFT (fast Fourier transformation) analysis of the yarn signal, thus permitting the detection even of minuscule periodic fluctuations that are not visible, for example, in the normal curve of yarn tension over time. The use of high scanning rates, for example of 50 kHz or 250 kHz, prevents the occurrence of aliasing effects during the FFT analysis.

Since the method according to the invention includes the detection of a large number of measurement signals, it is also provided according to the invention to condition and partly evaluate the analog measurement signals, preferably at the site of measurement, for purposes of data compression, and then to transmit the digital results to a central computer for storage, computeraided overall evaluation and documentation. The evaluation can be performed by the reception or determination of amplitude spectra, autocorrelation functions, curves of yarn tension over time, mean values, standard deviations, coefficients of variation, scattering matrices, FFT analyses and/or amplitude histograms of the yarn signal, particularly the yarn tension signal.

Alternatively or additionally, the solution to the above problem lies in a method for detecting untextured or defectively textured yarn segments in textured filament yarns during the texturing process, in which the yarn thickness is determined optically or laser-optically and is then evaluated. The examination of yarn thickness provides, in an advantageous manner, information regarding the texturing process and the quality of the yarn obtained, since comparatively thin yarn locations that can be recognized by optic or laser-optic means indicate untextured or defectively textured yarn segments that have not been untwisted. According to the invention, deviations of yarn thickness greater than 20%, in particular, indicate short, untextured yarn locations. In particular, short tight spots could not be detected by the methods of prior art, but this can now be done in an advantageous manner by means of the present invention. Brief instabilities that cause tight spots, for example slippage of the yarn on a disk of the friction unit, can therefore be detected in an advantageous manner.

The invention also provides a method for detecting untextured or defectively textured yarn segments in textured filament yarns during the texturing process, in which the yarn position and/or variations of the yarn position, in particular fluctuations of the transverse travel of the yarn, are determined optically and/or laser-optically and evaluated. The use of optic or laser-optic devices makes it possible, in this embodiment of the invention as well, to detect brief instabilities that cause undesired brief disruptions. The present invention is therefore based, inter alia, on the realization that the position of the yarn or the variation of its position during travel over a disk surface of the twister preferably realized as a friction unit can be used to detect short, untextured or defectively textured yarn segments. In an especially preferable manner, it is provided according to the invention to determine the behavior of the yarn as it travels over the exit disk of the friction unit—i.e., the last friction disk, which is usually a yarn guide disk. In a stable texturing process, i.e., a texturing process in which no tight spots are formed, the yarn travels to the exit disk in a sharp curve, which indicates that a frictional force is acting on the yarn. The curvature of the path of travel of the yarn becomes smaller in a slightly unstable process, while in a very unstable process the yarn passes almost rectilinearly over the last disk, which indicates that the frictional force being exerted is tending toward 0. An unstable process is subject in particular to variations of the path of travel of the yarn on the exit disk that have a wave-like appearance. From this it will be appreciated that in an unstable process the yarn skips across the surface of the disk. This twist slippage causes a torque deficit in the twist zone. If this wave occurs on the exit disk, high-twist yarn can briefly pass through the unit without relaxation of the twist, and thereby form tight spots.

The optic or laser-optic examination of the travel behavior of the yarn, especially on the exit disk, therefore makes it possible to detect short tight spots in textured yarn. The detection of short untextured yarn segments by determining and evaluating the position and travel behavior of the yarn can be used, either alone or in combination with the yarn-thickness detection method described hereinabove, for the determination of short untextured yarn segments.

In an especially preferred manner, the present invention provides a method for detecting short, untextured or defectively textured yarn segments in textured filament yarns during the texturing process, which uses to determine both the thickness of the yarn and the position and/or travel behavior of the yarn, optic and/or laser-optic devices that are able to detect short tight spots in the yarn, i.e., that have high scanning rates, preferably >10 kHz. According to the invention, the scanning rates selected should in particular be so high that at the chosen production speed the yarn thickness is scanned at 1-mm intervals and fluctuations of yarn position of 6 kHz or more can be detected. The higher the scanning rates and the resolution of the optic and/or laser-optic devices used, the shorter the tight spots that can be detected and/or the higher the production speeds at which the method can be employed. The yarn thickness can be determined by means of a photocell and the variation of the yarn position by means of a photocell strip (CCD strip).

According to a further preferred embodiment of the invention, it is provided to perform both the determination of the yarn thickness and the determination of the position and/or travel behavior of the yarn during the imparting of the twist in the region of the friction disks of the disk friction unit, in particular to perform said determination on or at the last working disk or the last yarn guide disk, i.e., the exit disk. Depending on the instability of the texturing process, the travel behavior, in particular, of the yarn exhibits marked differences at or on the exit disk, and the optic or laser-optic measurements therefore are preferably to be performed there. However, the detection of the yarn thickness can also take place over the entire distance from the exit disk of the twister to the winding of the textured yarn onto the spool.

The described method according to the invention can also, of course, be used to detect long untextured yarn segments (so-called surging spots).

Further advantageous embodiments of the invention will be understood from the dependent claims.

Figure 2A:
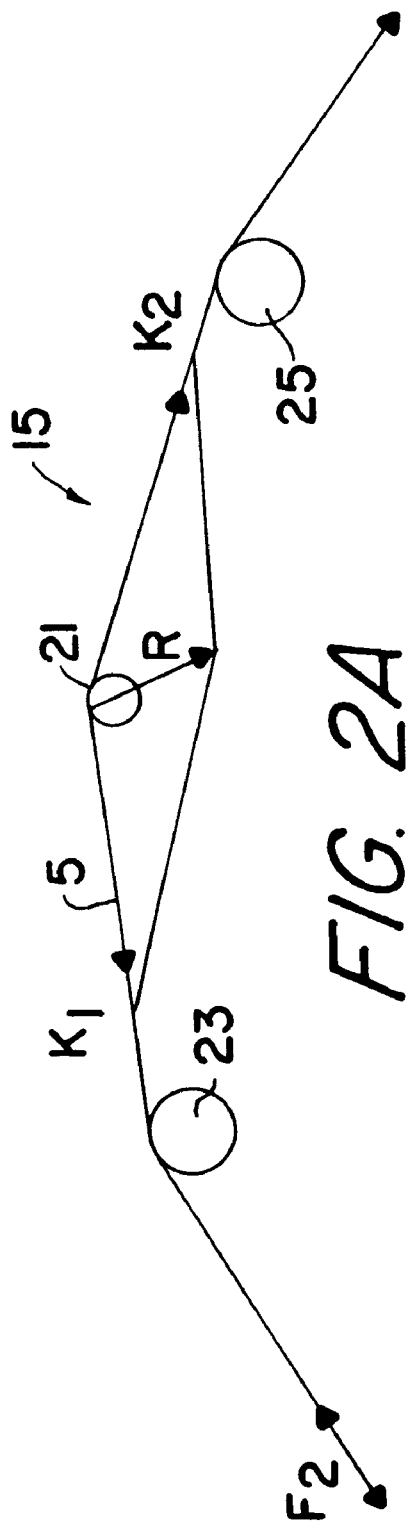
Figure 2B:
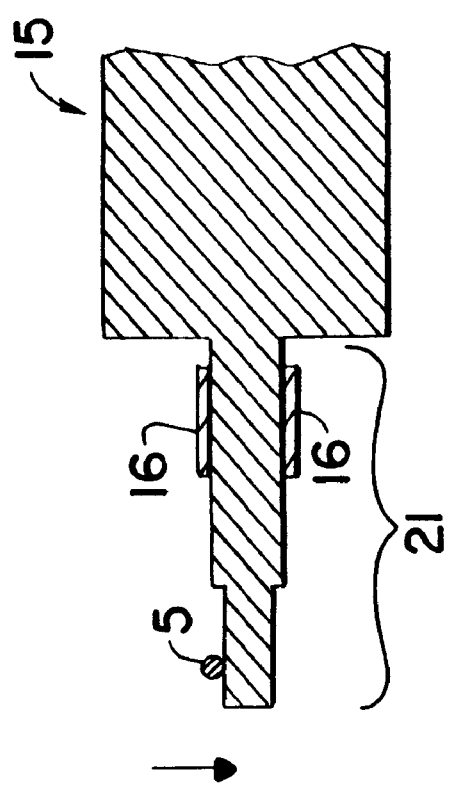
Figure 3:
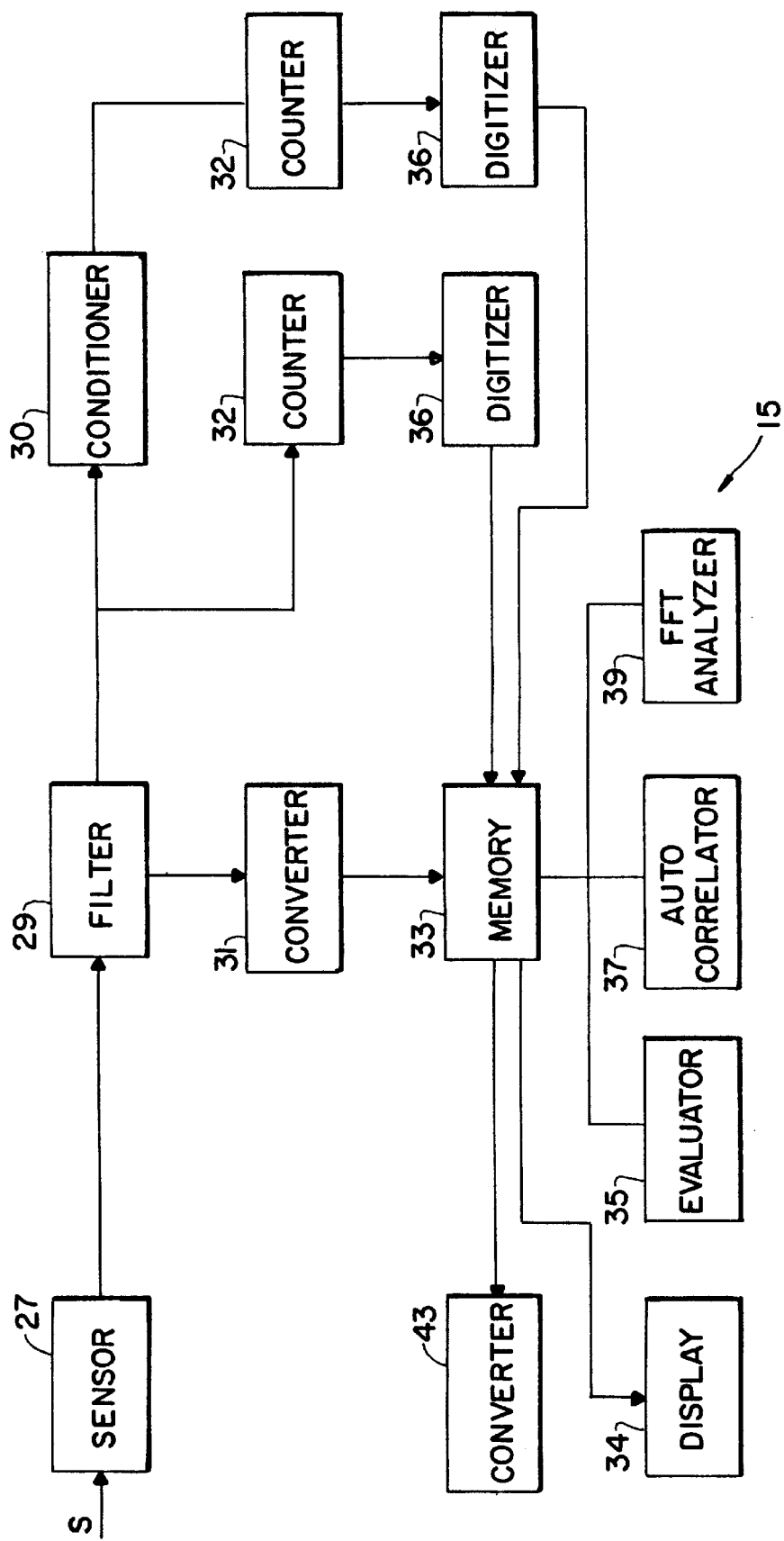
Figure 4A:
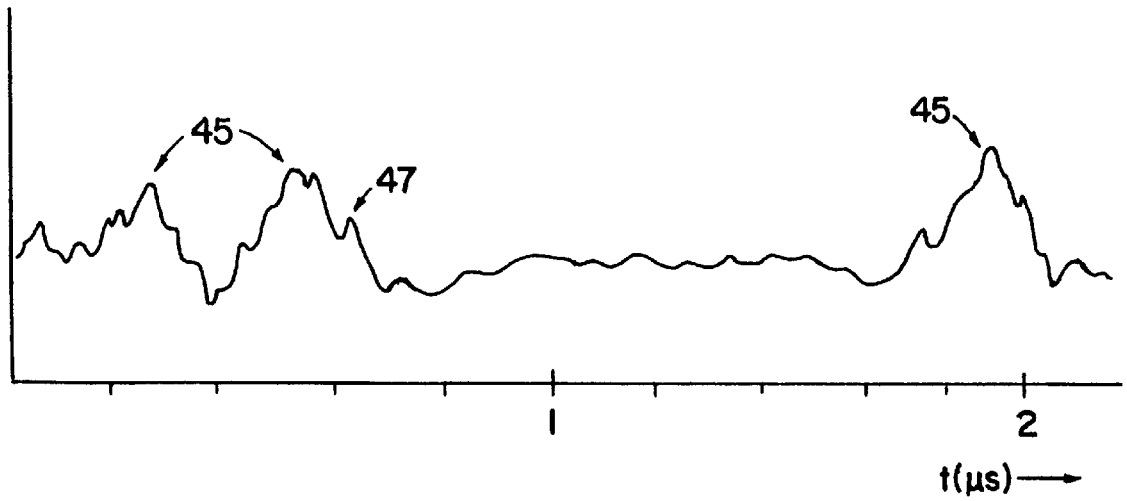
Figure 4B:
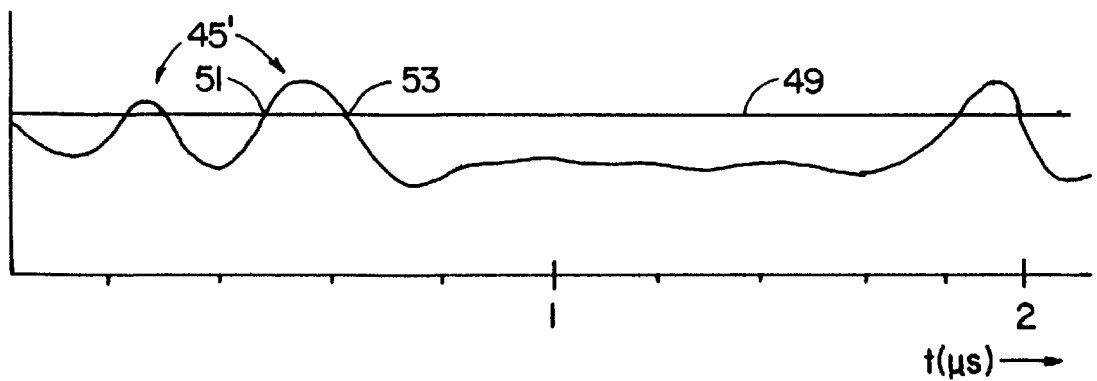
Figure 5A:
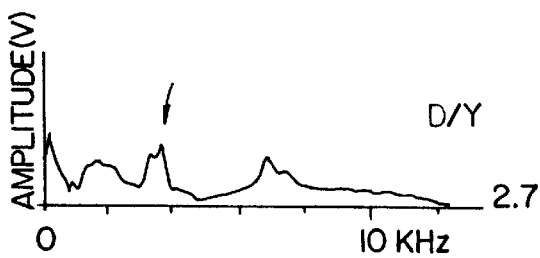
Figure 5D:
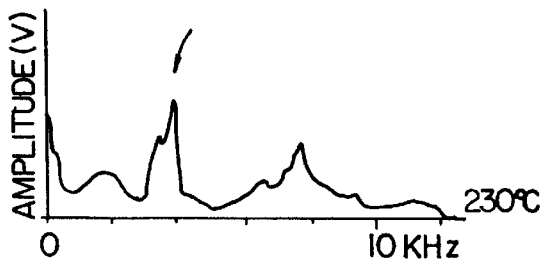
Figure 5B:
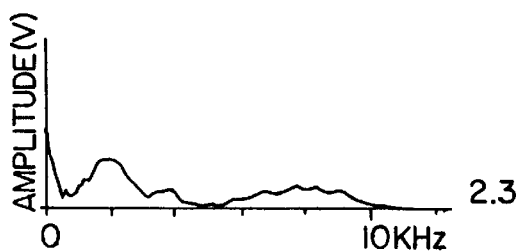
Figure 5E:
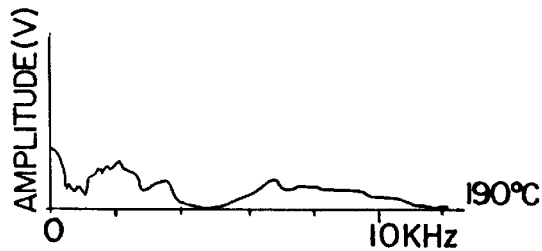
Figure 5C:
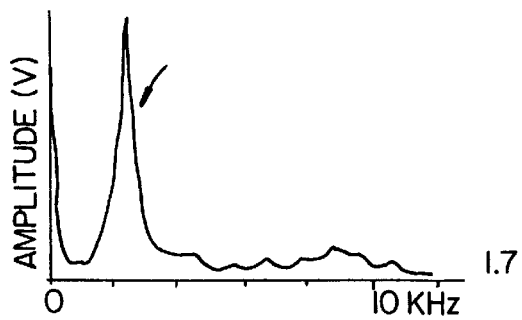
Figure 5F:
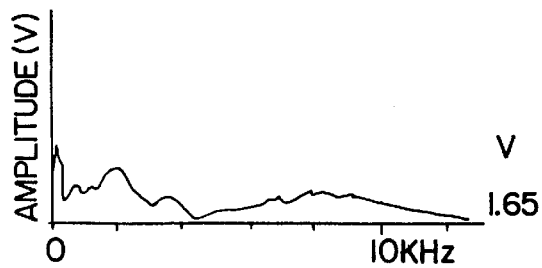
Figure 5G:
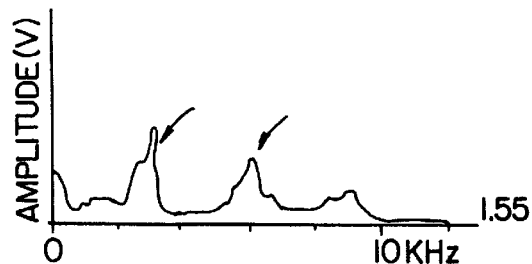
Figure 6:
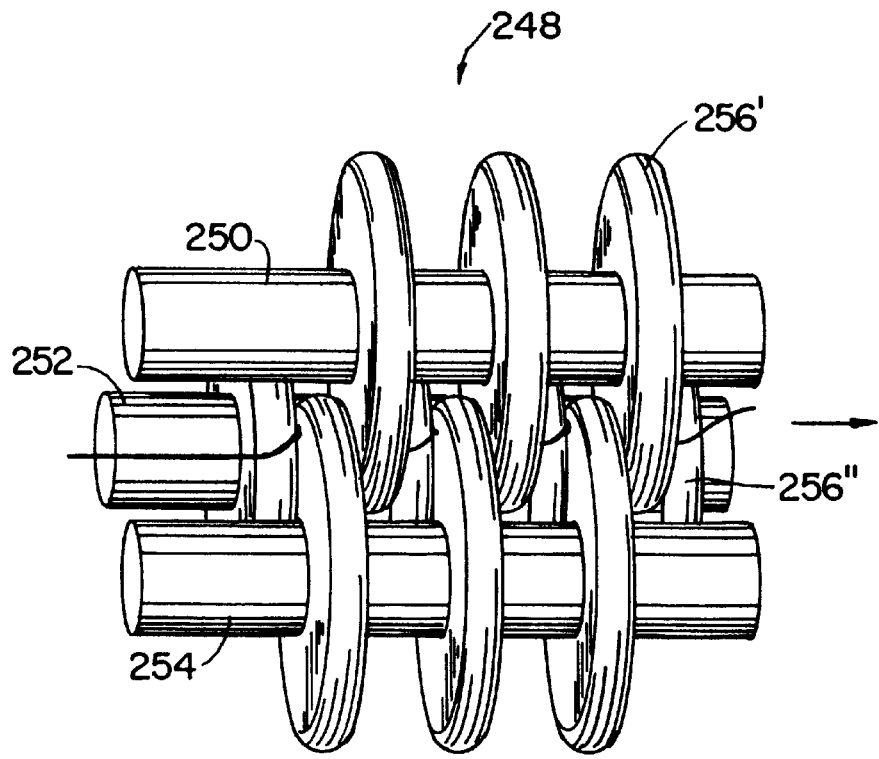
Figure 7:
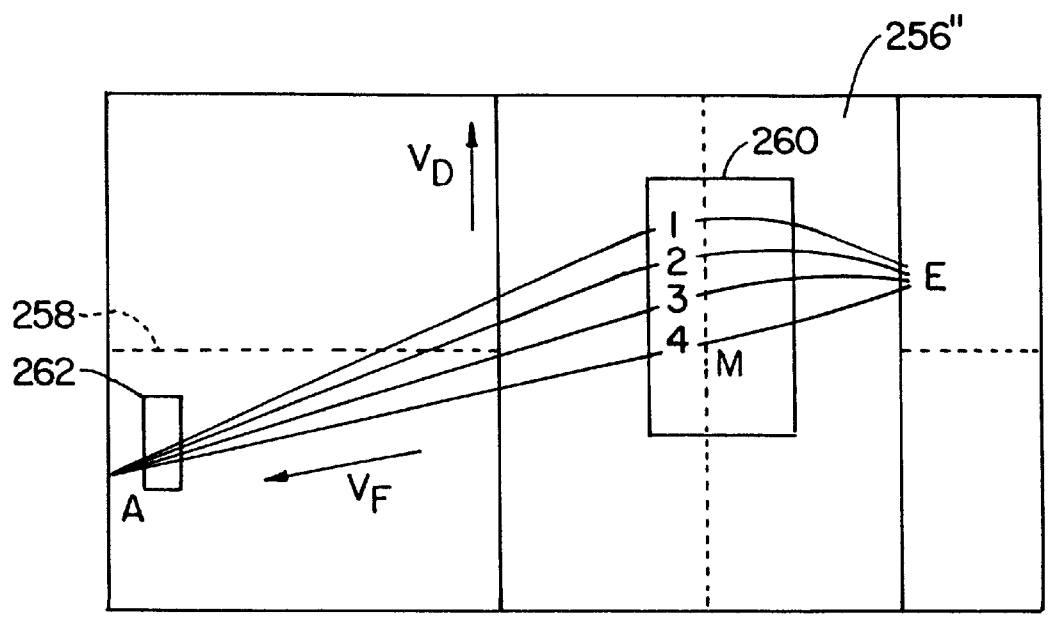

Further details, features and advantages based on the invention will emerge from the following description of exemplary embodiments, provided with reference to the drawings, which show, in:

FIG. 1 schematically, an arrangement for the texturing of multifilament yarns;

FIGS. 2A and 2B schematically, the principle of determination of the yarn tension;

FIG. 3 the structure of a device according to the invention in the form of a block diagram;

FIGS. 4A and 4B the curve of the yarn tension over time before and after the insertion of a low-pass filter and FIGS. 5A to 5G amplitude spectra of the yarn tension F2 after the twister in stable and unstable processes FIG. 6 a friction unit and FIG. 7 schematically, the travel geometry of the yarn on the exit disk of a friction unit.

FIG. 1 schematically illustrates a device 1 for texturing filament yarns by a friction false-twist method. The device 1 comprises a spool 3 from which the multifilament yarn 5 is unwound and guided through a delivery device 7 into a heater 9 [syntax sic]. The multifilament yarn 5 is guided out of the heater 9 over a cooling rail 11 and through a twister 13 realized as a disk friction unit into a draw-off delivery device 17 and from there to the yarn spool 19. Disposed between twister 13 and draw-off delivery device 17 is a device 15 for detecting unstructured, particularly untextured or defectively textured, yarn segments in textured filament yarns. It can also be provided according to the invention that device 15 is disposed downstream, i.e., after draw-off delivery device 17 and before yarn spool 19.

FIGS. 2A and 2B illustrate the basic structure of the monitoring device 15 and the force components K1 and K2 exerted on the yarn 5. Device 15, comprising measuring pin 21, wire strain gauge 16 and a measurement and evaluation system (not shown), measures the yarn tension F2 after twister 13 of the yarn 5 guided across measuring pin 21 and two guide pins 23, 25. The deflection of measuring pin 21 can be measured by means of wire strain gauge 16, Hall sensors, or capacitive, inductive or optical sensors. It will also be understood from FIG. 2A that the yarn 5 passes over guide pins 23, 25 and pin strain gauge 21, so that these are disposed inside the radius of curvature of the path of the yarn. In FIG. 2B, the bending direction of measuring pin 21 (bending beam) is indicated by an arrow. The bracket indicates the bendable region 21 of device 15, the wire strain gauges 16 being disposed in the region of potentially greatest deflection. Other measurement systems can, of course, be used to determine the yarn tension, provided that they are able to receive high-frequency yarn tension signals in the range of at least 0.2 kHz to 6 kHz.

FIG. 3 shows the structure of device 15 in the form of a block diagram. Device 15 comprises a measuring sensor 27, to which a buffer amplifier (not shown) can potentially be assigned. The signals S received by measuring sensor 27 and potentially amplified are routed through a filter 29, preferably a low-pass filter, to an analog-to-digital converter 31. The digitized signals are stored in a memory 33 and can be evaluated by means of suitable devices and methods, for example by the determination of means and standard deviations or the plotting of histograms (block 35), or by the performance of an autocorrelation (block 37) or an FFT analysis (fast Fourier transformation) (block 39). The data digitized by analog-to-digital converter 31 can also be routed to a digital display 34 or to a digital-to-analog converter 43. To compress the data sets, it is advantageous to a condition the analog measurement signal (S) or the filtered signal electronically by analog means, for example by analog differentiation, taking of the mean, determination of the scattering matrices (block 30) and/or the setting of selectable thresholds for counting the number of excursions over the threshold value (block 32). The digitized results of the count (block 36) already represent extreme compression of the data set and can be delivered to a central evaluating computer for storage (block 33) and for further processing and hard-copy printout or display (block 34).

Said signal processing devices can comprise devices for the selectable setting of threshold values and counting devices that determine the number of high-frequency yarn tension signals exceeding the threshold value per time unit and supply this number as a measure of the degree of crimping of the yarn and of irregularities and tight spots.

The operation of the device can be described as follows. The smooth multifilament yarn 5 on spool 3 is guided through delivery device 7, heater 9, cooling rail 11 and twister 13. Twister 13, which can be realized as a disk friction unit, for example, twists the filament yarn, causing the turns to "pile up" in the upstream direction, i.e., the direction of delivery device 7. The twisted filament yarns are in a state of tension that is heat-set by heating in heater 9, for example to 200° C., and cooling on cooling rail 11. As soon as the yarn 5 leaves twister 13, the torque is again removed from the yarn 5, although at least some of the state of tension of the yarn 5 obtained by the heat-setting remains and causes the yarn leaving twister 13 to be crimped, structured, bulky and lofty. This yarn is guided through device 15 and a draw-off delivery device 17, and after leaving-draw-off delivery device 17 in the relaxed state, can be wound onto yarn spool 19.

The method according to the invention now provides for the localization in particular of short tight spots in the yarn 5, i.e., short, untextured segments of yarn, thereby providing a statement as to the degree and evenness of crimping of the yarn. Such short tight spots in the yarn 5 are manifested by brief yarn tension signals. The method according to the invention permits the determination and evaluation of the crimping of the yarn through the detection of high-frequency—i.e., brief—yarn tension signals. For this purpose, the twisted yarn 5 is guided over the guide pin 23 shown in FIG. 2 to a measuring pin 21 comprising, for example, one or more, for example two or four, wire strain gauges. The yarn 5 is then routed over a further guide pin 25 to draw-off delivery device 17. Measuring sensor 27 realized as a measuring pin has, for example, a periodic resonance preferably in excess of 6 kHz, especially preferably in excess of 10 kHz, permitting the reception of high-frequency yarn tension signals in frequency ranges of 0.2 to 6 kHz or 0.2 to 10 kHz. Such yarn tension signals can, for example, be measured and analyzed at a scanning rate of 250 kHz (FIG. 5).

FIG. 4A shows a curve of yarn tension F2 over time (compare FIG. 2) for a yarn 5 exiting twister 13. The high-frequency yarn tension signals 45 shown indicate short tight spots in the yarn 5.

The high-frequency yarn tension signals 45 received are smoothed by means of a low-pass filter whose resonance is, for example, approximately 60% of the periodic resonance, so that it filters out (FIG. 4B) the extremely high-frequency yarn tension signals 47, for example above 10 kHz, caused by vibrations of the yarn 5 on the friction disk. FIG. 4B further shows that a threshold value 49 is set for the evaluation of the signals obtained; a counting device registers the number of yarn tension signals 45' exceeding the threshold value 49 per time unit (threshold excursions 51, 53). The number of yarn tension signals exceeding threshold value 49 per time unit provides information on the existence of short tight spots in the yarn 5.

The described method according to the invention and the device for carrying out this method can also, of course, be used to detect longer untextured yarn segments (surging spots) on the yarn 5.

FIGS. 5A to 5C show amplitude spectra of the yarn tension F2 with different D/Y ratios (D: circumferential speed of the disk; Y: speed of the yarn). D/Y ratios of 1.9 to 2.5 (FIG. 5B) indicate the presence of a stable process in which no tight spots are produced, whereas in the ranges D/Y<1.9 and >2.5, tight spots occur (FIGS. 5A and 5C). High amplitudes characteristic of short tight spots are marked with an arrow.

FIGS. 5D and 5E show amplitude spectra of the yarn tension F2 at different heater temperatures, taking as an example a microfilament yarn PES 50 dtex f80. At a heater temperature of 230°, amplitudes of fluctuation of the yarn tension (FIG. 5D) occur, especially in the high-frequency range, that result in tight spots and filament breakage. High heater temperatures cause an unstable process, recognizable by the high-frequency fluctuations of the yarn tension, and therefore result in damage to the yarn. FIG. 5E illustrates the amplitude spectrum of a stable process at a heater temperature of 190° C.

FIGS. 5F and 5G show amplitude spectra of the yarn tension F2 with different degrees of stretch V. With low stretch (V=1.55), tight spots are formed; at a degree of stretch V=1.60 a stable process is present[3].

[3]TRANSLATOR'S NOTE: Last clause of sentence garbled (" . . . at which degree of stretch of V=1.60 is a stable process are present.")

FIG. 6 schematically depicts the structure of a twister 13 realized as a friction unit 248. FIG. 6 illustrates the structure of the disk friction unit 248 comprising three shafts 250, 252, 254. Disposed on each of the three shafts 250, 252, 254 are concentric friction disks 256. The direction of travel VF of the yarn is indicated by an arrow. The determination according to the invention of the thickness or travel behavior of the yarn is preferably performed at or on the last working disk 256' or the exit disk 256".

FIG. 7 schematically illustrates the geometry of the path of travel of the yarn on exit disk 256" under different process conditions. The figure shows the path of travel of the yarn in direction VF from entry point E over exit disk 256" with its equator M (the center of the disk) in the direction of exit point A of unit 248. The axis 258 of the disk is also shown. The travel behavior and/or thickness of the yarn on exit disk 256" is determined by means of a high-speed video camera with an evaluating system and the ability to receive up to 6000 images/s. The optic or laser-optic determination of the thickness and/or travel behavior of the yarn can be performed on (block 260, for example) or after (block 262, for example) exit disk 256". The images taken by the high-speed video camera reveal that the yarn moves essentially perpendicular to its direction of travel VF on disk 256", i.e., in the direction VD, during both stable processes and unstable processes, that is, texturing processes that result in tight spots. In a stable process—i.e., a process in which no tight spots occur—the yarn traces a sharp curve (Position 1). The amplitude of the transverse movement of the yarn is small. The maximum amplitude of the transverse movement of the yarn at the center M of the disk is app. 0.2 mm (the diameter of the PES yarn 50 dtext f80 in the friction unit is 0.09 mm, and the travel speed of the yarn is, for example, 600 m/min).

In a slightly unstable process there is relatively large transverse movement of the yarn, the maximum amplitude of said transverse movement being 0.5 mm. The yarn oscillates periodically at a low frequency back and forth between Positions 1 and 3.

In a frankly unstable process, the yarn is usually in Position 4. The yarn oscillates periodically at a low frequency back and forth between Positions 4 and 2, the maximum amplitude of the transverse movements of the yarn being app. 1 mm.

Undesired short, untextured locations in the yarn (tight spots) occur when the process is unstable.

Since tight spots can also be detected in textured yarn by measuring the yarn tension in the kHz frequency range, the optical method according to the invention can be used to check or replace yarn tension measurements. According to the invention, results concerning the travel behavior of the yarn or the yarn thickness can be correlated with the results of yarn tension measurement in order to detect tight spots. At higher yarn tensions, the yarn tends to follow a rectilinear, more gently curved path over disk 256'', i.e., it tries to take the shortest route. In so doing, the yarn can, for example, slip from Position 1 to Position 2, thereby giving rise to twist slippage and undesired tight spots. The yarn thickness varies little in Zone M-A (see FIG. 7) during a stable process, whereas an unstable process is recognizable by a fluctuating yarn thickness with the formation of short tight spots.

The method according to the invention can, of course, be used to detect not only short tight spots, but also long, untextured segments of yarn (surging spots).

What is claimed is:

1. A method for detecting untextured and defectively textured yarn segments in textured filament yarns, during a texturing process, the textured yarn being measured continuously, said method comprising generating and measuring high-frequency yarn tension measurement signals in a frequency range of 0.2 to 10 kHz, conditioning the measurement signals as evidence of untextured and defectively textured yarn segments, and evaluating the degree and evenness of crimping of the yarn.

2. The method according to claim 1, wherein said method comprises generating and measuring the high-frequency measurement signals in a frequency range of from 1 to 6 kHz.

3. The method according to claim 1, wherein measuring, conditioning, and evaluating the high-frequency yarn tension signals for evidence of untextured and defectively textured yarn segments.

4. The method according to claim 3, wherein conditioning the measured yarn tension signals occurs prior to evaluating the signals.

5. The method according to claim 3, further comprising filtering out the yarn tension signals with frequencies above 6 kHz.

6. The method according to claim 3, wherein the texturing process is a friction false-twist process.

7. The method according to claim 3, wherein measuring the yarn tension signals occurs after the filament yarn has passed through a twister.

8. The method according to claim 3, wherein the filament yarn is composed of a thermoplastic material.

9. The method according to claim 3, wherein evaluating the high-frequency measurement signals is accomplished by determining a mean, a standard deviation, a number of times a threshold value is exceeded, and plotting of at least one of an amplitude histogram, an amplitude spectrum, a fast Fourier transformation analysis, and an autocorrelation.

10. The method according to claim 1, wherein by a selected one of optically determining and laser-optically determining a selected one of yarn thickness and deviation from a mean yarn thickness, and then evaluating the selected one of yarn thickness and deviation from a mean yarn thickness.

11. The method according to claim 10, wherein by the selected one of optically determining and laser-optically determining position and travel behavior of the yarn, including transverse movement thereof, and evaluating the position and travel behavior of the yarn.

12. The method according to claim 10, further comprising detecting short, untextured yarn segments.

13. The method according to claim 10, wherein the selected one of optically determining and laser-optically determining is performed by means of devices having high scanning rates above 10 kHz.

14. The method according to claim 10, further comprising performing by the selected one of optically determining and laser-optically determining the selected one of yarn thickness and deviation from a mean yarn thickness during imparting of twist effected during the texturing process, in the region of friction disks of a disk friction unit.

15. The method according to claim 10, further comprising performing by the selected one of optically determining and laser-optically determining the selected one of yarn thickness and deviation from a mean yarn thickness at the exit disk of a disk friction unit.

16. The method according to claim 10, further comprising performing by the selected one of optically determining and laser-optically determining the selected one of yarn thickness and deviation from a mean yarn thickness on a segment between a twister and a yarn wind-up spool.

17. The method according to claim 10, further comprising correlating the results of the selected one of optically determining and laser-optically determining the selected one of yarn thickness and deviation from a mean yarn thickness with results of yarn tension measurements and evaluating the correlation.

18. A device for detecting untextured and defectively textured yarn segments in textured filament yarns, the device comprising a sensor adapted to receive yarn tension signals at high frequencies in a range of 0.2 to 10 kHz, an apparatus for storing a threshold-value, and a counting device for determining the number of yarn tension signals that exceed the threshold value in a set period of time.

19. The device according to claim 18, wherein the sensor further comprises a bendable measuring pin over which the yarn can be guided, and deflection of the measuring pin is measured by a selected one of a wire strain gauge, Hall sensor, capacitive sensor, inductive sensor and optical sensor.

20. The device according to claim 18, wherein a filter is arranged between the sensor and the apparatus for storing a threshold-value.

21. The device according to claim 18, comprising electronic analog means to condition the measurement signal of the sensor for data compression.

22. A device according to claim 21, wherein said conditioning means comprise analog differentiation, taking of the mean, determination of the scattering matrices and/or the setting of selectable thresholds for counting the number of excursions over the threshold-value.

* * * * *